United States Patent [19]

Fujioka et al.

[11] Patent Number: 5,011,692

[45] Date of Patent: Apr. 30, 1991

[54] SUSTAINED PULSEWISE RELEASE PHARMACEUTICAL PREPARATION

[75] Inventors: Keiji Fujioka; Shigeji Sato; Yoshihiro Takada; Yoshio Sasaki; Nobuhiko Tamura, all of Ibaraki, Japan

[73] Assignee: Sumitomo Pharmaceuticals Company, Limited, Osaka, Japan

[21] Appl. No.: 946,158

[22] Filed: Dec. 23, 1986

[30] Foreign Application Priority Data

Dec. 28, 1985 [JP]  Japan .................. 60-297550
Nov. 14, 1986 [JP]  Japan .................. 61-272542

[51] Int. Cl.$^5$ .................................. A61F 2/00
[52] U.S. Cl. ........................... 424/426; 424/425; 424/484; 424/485; 424/486
[58] Field of Search ............ 424/484, 485, 486, 425, 424/426; 604/892.1

[56] References Cited

U.S. PATENT DOCUMENTS

| | | | |
|---|---|---|---|
| 4,217,898 | 8/1980 | Theeuwes | 424/486 X |
| 4,359,483 | 11/1982 | Kaetsu | 427/2 |
| 4,439,196 | 3/1984 | Higuchi | 604/892.1 X |
| 4,559,054 | 12/1985 | Bruck | 424/486 X |
| 4,564,364 | 1/1986 | Zaffaroni et al. | 424/484 |
| 4,627,850 | 12/1986 | Deters et al. | 604/892.1 |
| 4,663,147 | 5/1987 | DePrince | 424/486 X |

FOREIGN PATENT DOCUMENTS

| | | |
|---|---|---|
| 0062391 | 10/1982 | European Pat. Off. . |
| 0138216 | 4/1985 | European Pat. Off. . |
| 2100858 | 3/1972 | France . |
| 120618 | 9/1981 | Japan . |
| 57-126415 | 8/1982 | Japan . |
| 13466092 | 2/1974 | United Kingdom . |

OTHER PUBLICATIONS

Langer, *Journal of Membrane Science*, 7, 333-350, 1980.

*Primary Examiner*—Richard D. Lovering
*Assistant Examiner*—John M. Covert
*Attorney, Agent, or Firm*—Berman, Aisenberg & Platt

[57] ABSTRACT

The invention relates to sustained pulsewise release pharmaceutical preparation which comprices drug-containing polymeric material layers (layers A) and polymeric material layers containing the drug in question only in a slight amount or free of the drug (layers B) disposed alternatingly, with the whole surface extending in the direction perpendicular to the layer plane being coated with a polymeric material which is insoluble in water or scarcely soluble in water (polymeric material C).

This pharmaceutical preparation of this invention is designed so that active ingredients which should desirably be released pulsewise can be released therefrom in a pulse-like and clinically significant manner and thereby the pharmacological effects of said active ingredients can be maintained for a prolonged period of time.

20 Claims, 3 Drawing Sheets

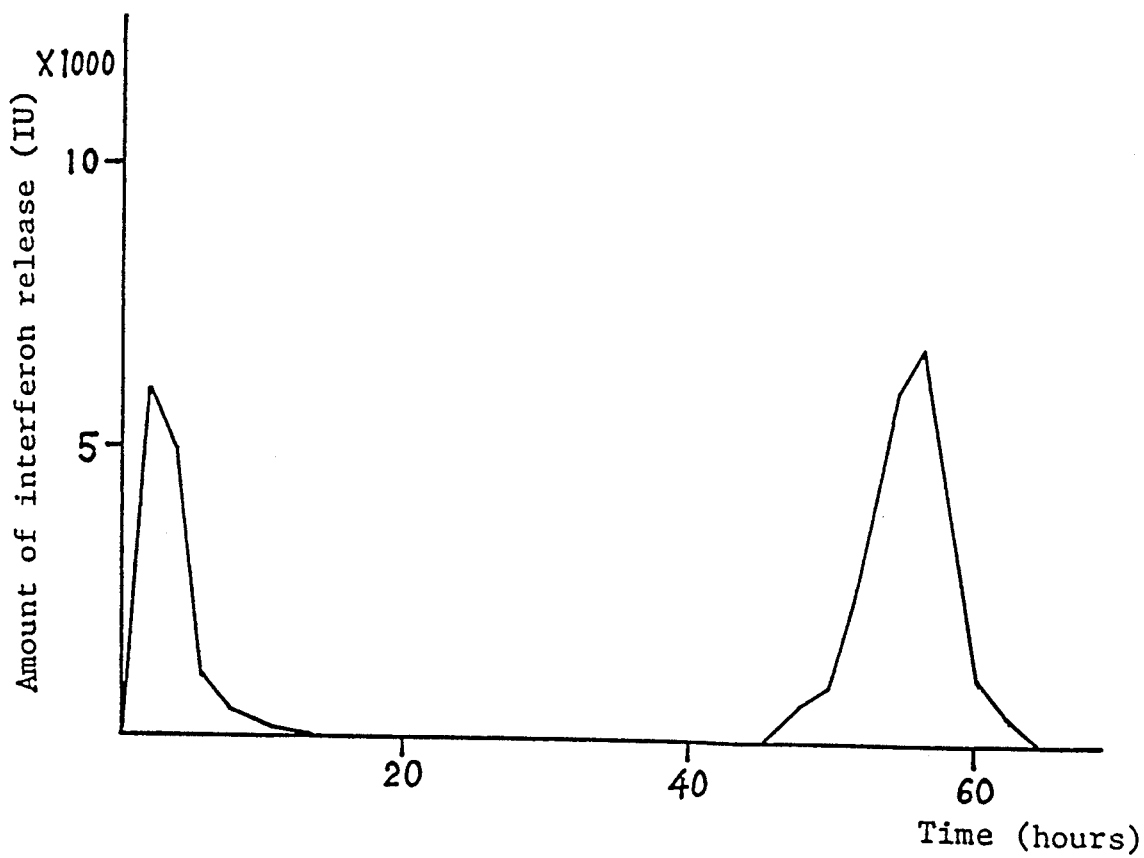

SUSTAINED PULSEWISE RELEASE PHARMACEUTICAL PREPARATION

BACKGROUND OF THE INVENTION

This invention relates to sustained release pharmaceutical preparations capable of releasing active ingredients sustainedly and in a pulse-like manner. More particularly, the invention relates to sustained release pharmaceutical preparations designed so that active ingredients which are desirably released pulsewise, such as biologically-active trace substances [e.g. peptide protein type active substances (e.g. hormones, cytokines), postaglandins, steroids, vitamins and the like], other active trace substances, anticancer agents and antibiotics, can be released therefrom in a pulse-like and clinically significant manner and thereby the pharmacological effects of said active ingredients can be maintained for a prolonged period of time.

Hithertofore various dosage forms and systems have been designed in an attempt to attain sustained release of drugs in a manner such that the drug concentrations can be maintained at clinical therapeutic levels. They bring sustained release to many kinds of drugs. However, as far as biologically-active trace substances, such as peptide protein type active substances (e.g. hormones, cytokines), prostaglandins, steroids, vitamins and the like, are concerned, the conventional modes of administration which allow continuous drug release are not always appropriate, since, in living organisms, said substances are to be released in a pulsating or pulse-like manner and living organisms have a function to suppress effect of such substance in case of giving them from inside or outside over the physiological level.

For example, it is known that luteinizing hormone (LH) is secreted in ovarectomized rhesus monkeys at about 60-minute intervals [Endocrinology, 87, 850-853 (1970)] and that, in rats, physiologically, growth hormone is secreted at intervals of about 3.5 hours [Endocrinology, 98, 562 (1976)]; it is also known that negative feedback is involved in the mechanisms of regulation of growth hormone (hGH) secretion, and it is reported that, in rats, administration of GH causes decreases in pituitary weight and GH content and an increase in somatostatin quantity in the hypothalamus [Life Sci., 24, 1589 (1979)]. Therefore, artificial continuous administration of such substances in large quantities is undesirable to living organisms in many cases.

Pulsewise administration of anticancer agents, antibiotics and the like is also desirable in certain cases. In particular, in the case of multiple drug therapy, pulsewise administration of several drugs differing in site of action in an effective order, for instance, can be expected to produce excellent effects in respect of efficacy, tolerance and reduced toxicity. From such viewpoint, pulsewise administration of drugs has been attempted.

Thus, for example, Langer et al. [J. Membrane Sci., 7, 333 (1980)] propose a pharmaceutical preparation for drug release by magnetic stirring, which comprises a drug substance and magnetic beads mixedly incorporated in a polymer (ethylene-vinyl acetate copolymer) matrix. Drug release is caused by vibrating the magnetic beads in the matrix by means of an external magnet. This preparation is indeed advantageous in that pulsewise drug release can be effected by actuating the external magnet intermittently, but the patient is restricted in his or her liberty by an external apparatus including said magnet. Moreover, continuous release at a certain rate is inevitable for structural reasons even when magnetic vibration is not effected, so that completely pulsewise release cannot be achieved.

Accordingly, an attempt has been made to attain liberation from external elements, decrease in complexity, and more complete pulsewise release. Thus, a sustained release composite preparation having a multilayer structure as disclosed by Kaetsu et al. (specification of Japanese Patent Application laid open under No. 120618/81) can attain pulsewise drug release in an intrinsic and simple manner without using any external apparatus. Said preparation comprises alternatingly disposed drug-containing and drug-free layers, for example drug-containing layers and drug-free layers for envelopment of each drug-containing layer.

From the viewpoint of precise pulsewise release, however, such technique has room for improvement. There is a fear that in case of the sperical, cylindrical or sheet-type preparation, (disclosed in the specification of Japanese Patent Application laid open No. 120618/81) the release pulse becomes vague due to irregular erosion and diffusion.

SUMMARY OF THE INVENTION

Accordingly, it is an object of the invention to provide a pharmaceutical preparation with which vaguely pulsewise drug release due to irregular erosion and diffusion can be avoided.

The invention thus provides a sustained pulsewise release pharmaceutical preparation which comprises drug-containing polymeric material layers (hereinafter referred to as "layers A") and polymeric material layers containing the drug in question only in a slight amount or free of the drug (hereinafter referred to as "layers B") disposed alternatingly, with the whole surface extending in the direction perpendicular to the layer plane being coated with a polymeric material which is insoluble in water or scarcely soluble in water (hereinafter referred to as "polymeric material C").

BRIEF DESCRIPTION OF THE DRAWINGS

In the accompanying drawings,

FIG. 4 and FIG. 5 each shows the results of testing of a pharmaceutical preparation according to the invention for pulsewise drug release pattern.

Figure 1:
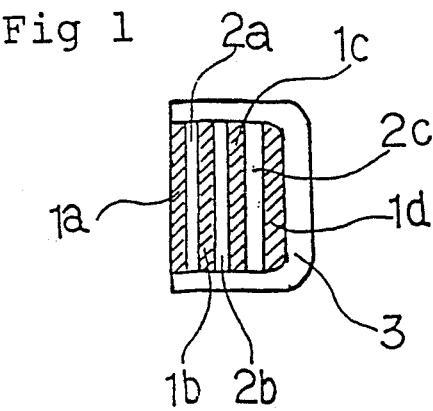
FIG. 1, FIG. 2 and FIG. 3 each shows, in section, an embodiment of the pharmaceutical preparation according to the invention.

1a, 1b, 1c, 1d, . . . layers A
2a, 2b, 2c, . . . layers B
3, 3', 3", . . . Coating layers

DETAILED DESCRIPTION OF THE INVENTION

The material to be used in forming layers A in acordance with the invention is not limited to any particular species but may be any polymeric material which is degradable in living organisms within a certain appropriate period of time and the drug contained therein is released in living organisms. Examples of such material are collagen, gelatin, polylactic acid, polyglycolic acid, poly(lactide-co-glycolide), silicone polymer and polyvinyl acetate.

The polymeric material for forming layers B may likewise be any polymeric material capable of being degraded in living organisms within a certain appropriate period of time and includes, among others, those examples mentioned above for layers A.

The polymeric material of layers A and that of layers B may be either the same or different.

The polymeric material C is not limited to any particular species but may be any polymeric material which is insoluble or scarcely soluble in water and in body fluids and is physiologically acceptable and can continue to serve as a coating for the laminated structure composed of layers A and layers B until disintegration of said layers A and layers B in living organisms is complete. Examples of such material are silicone polymers and polyvinyl acetate. From the viewpoint of ease in handling, thermal stability of drug substances, etc., silicone polymers are particularly preferable.

Suitable examples of the silicone polymers are methypolysiloxane, dimethylpolysiloxane, dimethylmethylvinylpolysiloxane and trifluoropropylmethylpolysiloxane. In particular, there may be mentioned dimethylpolysiloxane species represented by the formula

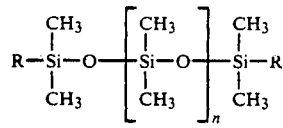

wherein n is 100-5,000 and R is methyl, hydroxy or vinyl, such as Dow Corning's Dow Corning® 360, Silastic® 382 and Dow Corning® MDX-4-4210, and methylvinylpolysiloxane species having the formula

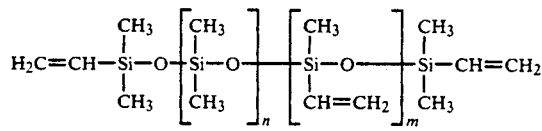

wherein n is 100-10,000 and m is 1-100, such as Dow Corning's Silastic® Medical Grade ETR. These silicone polymers are used in the elastomer form.

Thus, the starting material silicone polymer (silicone elastomer base) to be used in accordance with the invention generally occurs in a fluid or viscous liquid form and, upon addition of a curing agent (e.g. stannous octoate, chloroplatinic acid), turns into a solid rubber-like elastomer (silicone elastomer) to form a coating portion of the pharmaceutical preparation according to the invention.

The starting material silicone elastomer bases mentioned by way of example may be used either singly or in combination. For example, silicone elastomer more appropriate in degree of curing can be formed by adding Dow Corning® 360 in an appropriate amount (e.g. 0-20%, preferably 5-15%, more preferably about 10%) to Silastic® 382.

The drug to be incorporated in the pharmaceutical preparation according to the invention is not limited to any particular species but may be any drug intended for pulsewise release and thus includes, among others, (1) biologically active trace substances exemplified by peptide protein type active substances, such as hormones [e.g. growth hormone (GH), growth hormone releasing factor (GRF), luteinizing hormone (LH), luteinizing hormone releasing hormone (LH-RH), insulin, glucagon], cytokines [e.g. interferons (IFN), interleukins (IL), colony stimulating factors (CSF), tumor necrosis factor (TNF), macrophage activating factor (MAF), macrophage migration inhibitory factor (MIF)] and others [e.g. platelet-derived growth factor (PDGF), insulin-like growth factors (IGFs), somatostatin (SS), epidermal growth factor (EGF), angiotensin, tissue plasminogen activator (t-PA), renin, calcitonin, enkephalin, erythropoietin (EPO)], prostaglandins, steroids and vitamins (e.g. vitamin D), (2) anticancer agents (e.g. mitomycin, adriamycin, cisplastin), (3) antibiotics (e.g. β-lactam antibiotics, eruthromycin, amphotericin, polymixin), and so on.

Two or more drugs may be used in combination. When two drugs are used together for instance, both drugs may be incorporated in layers A. Of course, it is possible to incorporate one drug in layers A and another in layers B. In the latter case, drug release as a whole becomes continuous but, for the respective drugs, the release is pulsewise. In the case of combined use of two drugs, it is further possible to incorporate them in layers A alternatingly, for example, a first drug in layer 1a, a second drug in layer 1b, the first drug in layer 1c and the second drug in layer 1d, as shown in FIG. 1. Referring to FIG. 1, it is also possible to incorporate four different drugs in layers A, namely: in layers 1a, 1b, 1c and 1d, respectively.

The mode of drug incorporation includes, among others, direct incorporation of a drug itself in polymeric material layers and incorporation of a drug enclosed in minute particles. In the former case, the drug incorporation can be effected, for example, by mere admixing of a drug with a polymeric material which is to constitute drug-containing layers, or by dissolving a drug in water, conducting lyophilization and mixing the lyophilizate with a polymeric material, or by dissolving a drug and a polymeric material together in water, followed by lyophilization. In the latter case, the drug incorporation can be realized, for example, by mixing a drug enclosed in minute particles with a polymeric material, or by suspending drug-containing microcapsules in a high concentration solution of a polymeric material followed by immediate lyophilization. No particular limitations are placed on the minute particles provided that said particles should meet the following requirements: that they should be pharmacologically acceptable, that the drug in question should be enclosable therein and that they should be disintegrable in body fluids to thereby release the drug enclosed therein. Preferable particle sizes generally lie within the range of about 17 nm to about 1,000 μm, preferably within the range of about 100 nm to about 100 μm. Concrete examples are liposome, microcapsules and microspheres.

Enclosure of a drug in minute particles results in stabilization of the drug, improved maintenance of the pharmacological effect or effects and a more definite pulse pattern.

Drug stabilization is particularly important when the active drug substance is an unstable protein, for instance. Localization resulting from enclosure in minute particles as well as close coexistence within minute particles with a stabilizer suited to the drug (e.g. albumin, cholesterol, sodium benzoate) can promote the stabilization. Enclosure in minute particles can prevent possible drug deactivation, for instance, resulting from interaction between two or more drugs contained in the same or different polymeric material layers or between a drug and the polymeric material or materials forming polymeric material layers.

The use of a drug enclosed in minute particles thus results in prolonged duration of drug efficacy, and said duration can be adjusted in connection with the intended pulse by selecting the kind and size of minute particles for drug enclosure.

When the drug is an active trace substance, for instance, it is very difficult to achieve definite pulsewise release of the drug in very small amounts. By enclosing such drug in minute particles together with a known vehicle and disintegrater (e.g. mannitol, sucrose, sodium hydrogen carbonate, starch, carboxymethylcellulose), however, it becomes possible to promote drug release and render the pulse more definite.

The method of preparing such drug-containing minute particles is not limited to any special one. Generally employable methods are described in J. Mol. Biol., 13, 238–252 (1965) and "Microcapsules-Manufacture, Properties and Applications (1977)", for instance. Drug-containing layers can be produced by admixing drug-containing microcapsules with a polymeric material, followed by layer formation.

The drug content in each layer may suitably be selected depending on the kind of drug, the kind of polymeric material, and so forth. Layers B may contain the drug, which is contained in layers A, in slight amounts. The term "in slight amounts" should not be construed strictly but is used to mean relative slightness as compared with the drug amount in layers A. Thus, when a drug which can produce its pharmacological effect or effects only in large doses is used, relatively large amounts in which the drug is contained in layers B fall within the meaning of the term "slight amounts" as used herein if said relatively large amounts are still slight when compared with the drug amounts in layers A.

The means of producing laminate-type pharmaceutical preparations by alternatingly disposing layers A and layers B is not particularly limited. Meanwhile, according to the description in the specification to Japanese Patent Application laid open under No. 120618/81, laminate-type pharmaceutical preparations are prepared by using thermal denaturation of naturally occurring polymeric material, by application of synthetic polymeric materials using an organic solvent or solvents, or by radiation-initiated polymerization of vinyl monomers. However, these methods have problems, for example, in that they cannot be applied to those cases in which the drug or drugs are unstable to heat or radiation or that residual organic solvents may cause adverse reactions. Therefore, the present inventors recommend the compression molding method as a method free from the problems involved in the production method described in the specification of Japanese Patent Application laid open under No. 120618/81. The proposed method comprises forming layers A and layers B by compression molding of the respective ingredient mixtures to give the pharmaceutical preparations according to the invention. In accordance with an embodiment of the method, a layer A is first formed by compression molding and then a layer B is formed on said layer A by compression molding, followed by repeated formation of a layer A and a layer B in the same manner. In accordance with another embodiment, layers A and layers B prepared separately in advance by compression molding are laminated together with or without preliminary appropriate adhesion. Thus, for instance, a powder-form polymeric material is compression-molded on a compression molding machine, preferably at a pressure of 100–2000 kg/cm$^2$. A mixed powder composed of a drug and a polymeric material is placed on the resultant layer and compression-molded in the same manner. These procedures are repeated until a laminate structure (laminate-type preparation) is obtained.

A pharmaceutical preparation in which layers A contain a drug and layers B contain another drug, for instance, can also be produced in the same manner as above.

In this way the pharmaceutical preparations according to the invention can be prepared in a simple and easy manner and at the same time inactivation of drugs and adverse reactions due to residual organic solvents can be prevented.

The pulse frequency or interval and the pulse width can be adjusted by varying the number of drug-containing layers and of drug-free layers (which may contain drugs in slight amounts), the thickness of each layer, and so forth. Said pulse parameters are suitably selected depending on the kind of drug, treatment schedule and physiological condition of the patient, among others.

The pharmaceutical preparations according to the invention can be obtained by coating the thus-obtained laminate-type preparations with a polymeric material C by a conventional method. For example, when said polymeric material C is a silicone elastomer, which is a typical example, such as Silastic ® 382 (Dow Corning), the silicone base and the catalyst stannous octoate (about 2 drops per 10 g of silicone base) are quickly mixed and the laminate-type preparations are immersed in the mixture or the mixture is applied to the laminate-type preparations in the manner of painting, whereby the coating is accomplished.

In the above coating step, all the surface extending in the direction perpendicular to the layer plane is coated. Preferably, one of the surfaces extending in the direction parallel to the layer plane (i.e. that face from which drug release is not intended) is also coated.

The pharmaceutical preparations according to the invention are embedded beneath the skin in a particularly preferred embodiment. Thus, the drug is released pulsewise from the face having no polymeric material coating (i.e. drug release face). In cases where a relatively short drug efficacy duration is sufficient, the preparations may be administered perorally.

Referring to the drawings, some examples of the pulsewise release pharmaceutical preparation according to the invention are now described.

FIG. 1 shows, in vertical section, an embodiment of the pulsewise release preparation according to the invention, in which a laminate-type preparation composed of alternatingly disposed layers A, namely layers (1a), (1b), (1c) and (1d), and layers B, namely layers (2a), (2b) and (2c), is coated with a layer (3) of a polymeric material C on the whole surface extending in the direction perpendicular to the layer plane and on the face which extends in the direction parallel to the layer plane and drug release from which is not intended. In this example, the following modes, for instance, may be mentioned: layers A (1a), (1b), (1c) and (1d) contain a drug X while layers B (2a), (2b) and (2c) contain no drug at all (mode 1); layers A (1a), (1b), (1c) and (1d) contain a drug X while layers B (2a), (2b) and (2c) contain another drug Y which is different from the drug X (mode 2); layers A (1a), (1b), (1c) and (1d) contain a drug X and layers B (2a), (2b) and (2c) contain the drug X in slight amounts (mode 3).

Figure 2:
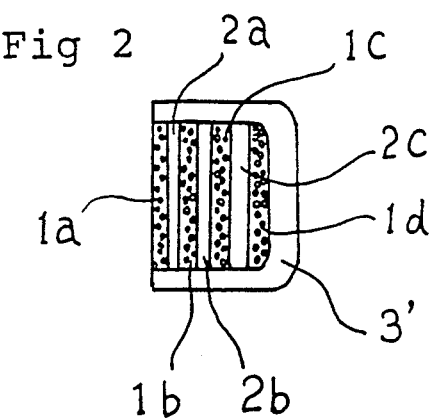

FIG. 2 shows the same embodiment as shown in FIG. 1 except that layers A contain the drug enclosed in minute particles.

Figure 3:
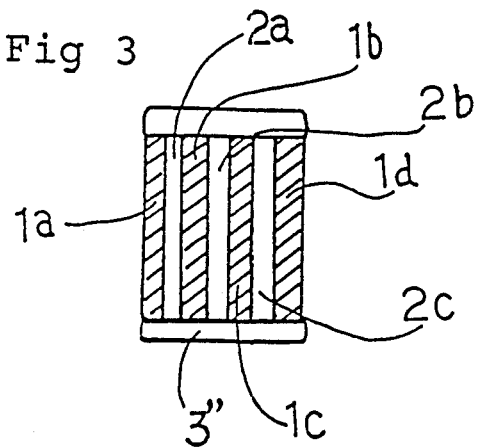

A further example shown in FIG. 3 is the same as that shown in FIG. 1 except that only the whole surface extending in the direction perpendicular to the layer plane is covered with a layer (3") of a polymeric material C, with both the faces extending in the direction parallel to the layer plane being free of such coating.

The geometry of the pharmaceutical preparation according to the invention is optional provided that said preparation is possessed of the constituent elements of the invention and that the object of the invention can be accomplished. For example, the preparation may be in the form of a cylinder, trigonal prism or tetragonal prism.

In the example shown in FIG. 1, the drug is released after administration of said pharmaceutical preparation from the layer (1a) and quickly gives a therapeutic concentration and then the drug release is discontinued. After the lapse of a certain time required for the dissolution of the layer (2a) or for the migration of the drug from the layer (1b) through the layer (2a), the drug contained in (1b) is released to quickly give a therapeutic concentration. The embodiment shown in FIG. 2 makes it possible to effect drug stabilization and to render the pulsewise release pattern more definite since the drug is contained in minute particles. In the embodiment shown in FIG. 3, the drug is released pulsewise from both the faces extending in the direction parallel to the layer plane.

EXAMPLE 1

Figure 4:
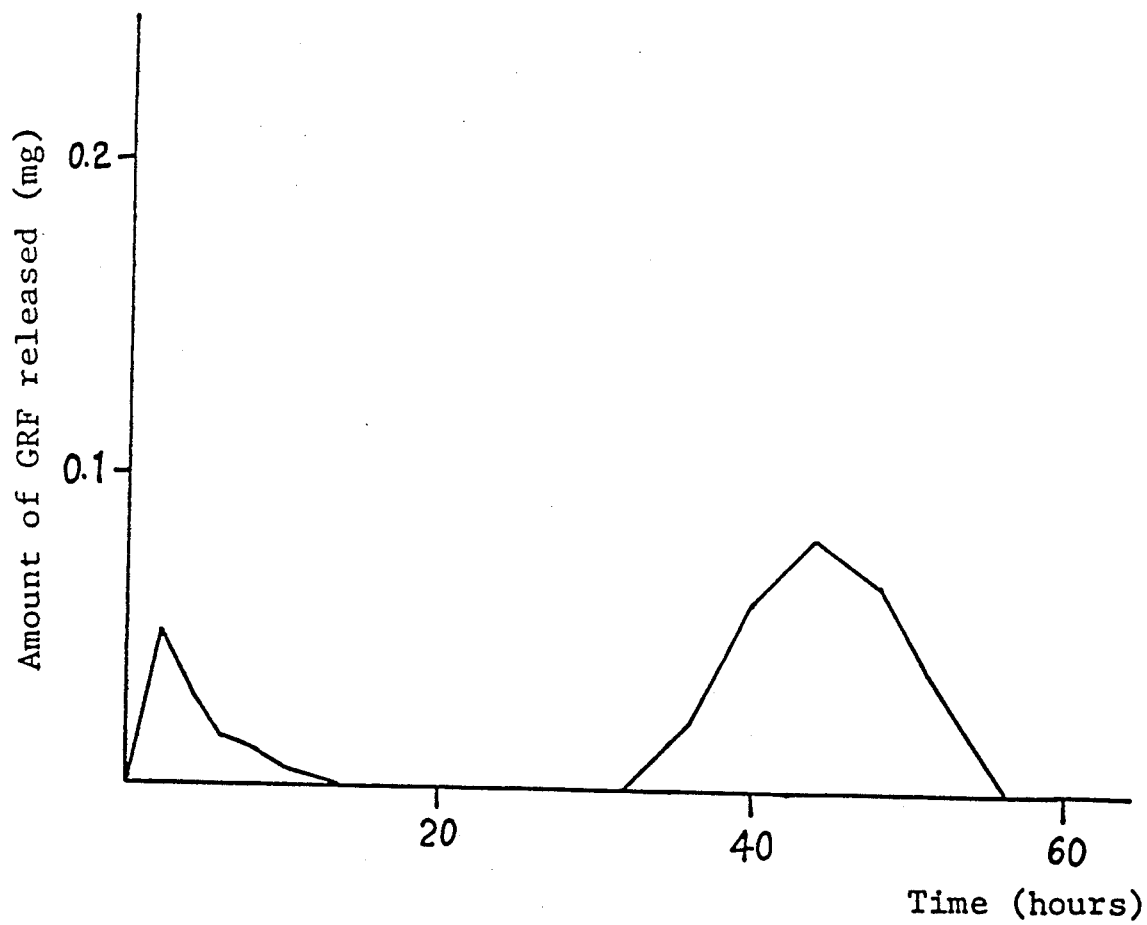

A mixture of 15 mg of atelocollagen and 1 mg of GRF (1-29) was compression-molded on a tableting machine (400 kg/cm$^2$) and 35 mg of atelocollagen was again compression-molded thereon. Thus were produced a GRF (1-29)-containing collagen layer and a GRF-free collagen layer. The above whole procedure was repeated three more times, so that four layers each were formed. A cylindrical pellet having a thickness of 1.3 mm, a diameter of 10 mm and a weight of 188 mg was thus produced. Separately, about 10 g of Silastic ® 382 silicone base and about 2 drops of stannous octoate were mixed together quickly. The mixture was placed in a vessel with a diameter of 15 mm and a depth of 5 mm. The above laminated cylindrical pellet was immersed in said mixture with the bottom (GRF-containing collagen layer) being left in contact with air. The silicone polymer was cured by allowing the mixture with the pellet immersed therein to stand at room temperature for 24 hours. Thereafter the whole was taken out of the vessel. The dissolution of GRF from the coated pharmaceutical preparation thus obtained was determined using physiological saline at room temperature and sampling the saline at timed intervals for determining the quantity of GRF released within a unit time by high-performance liquid chromatography. The results obtained are shown in FIG. 4.

EXAMPLE 2

Preparation of interferon-containing gelatin microspheres

Gelatin (2.5 g) was dissolved in 37.5 ml of water and, at 40° C., 5 ml of an α-interferon solution (about 3 MU/ml) was added with stirring. Further, at the same temperature, 50 ml of warmed ethanol (40° C.) was added dropwise. After completion of the dropping, the reaction mixture was poured into 500 ml of cooled 30% ethanol (5° C.) with stirring and the whole mixture was stirred for 30 minutes. The precipitate was collected by centrifugation and cooled to 5° C.

The precipitate was added to 500 ml of isopropanol, the mixture was stirred for 20 minutes, and the solid matter was collected by filtration using a glass filter, washed with 500 ml of cold ethanol and then dried to give about 1 g of interferon-containing microspheres. Radioimmunoassay revealed that this product contained 3710 U/mg of α-interferon.

Preparation of pulsewise release preparation

A 4-mg portion of the above α-interferon-containing gelatin microspheres was admixed with 15 mg of atelocollagen. The mixture was compression-molded on a tableting machine (400 kg/cm$^2$) and 35 mg of atelocollagen was again compression-molded thereon, whereby a collagen layer containing the α-interferon-containing gelatin microspheres and a collagen layer free of such microspheres were formed. After three more repetitions of the above double molding process, there was obtained a cylindrical pellet having a thickness of 1.3 mm, a diameter of 10 mm and a weight of 198 mg and composed of four drug-containing layers and four drug-free layers. Then, in the same manner as in Example 1, the pellet was coated with the same silicone polymer except for one release face (collagen layer containing the α-interferon-containing gelatin microspheres). The thus-obtained pharmaceutical preparation was tested for dissolution of α-interferon therefrom at ordinary temperature using PBS buffer containing 0.5% human serum albumin. Sampling was made at timed intervals and the quantity of α-interferon released within a unit time was determined by radioimmunoassay. The results obtained are shown in FIG. 5.

The pharmaceutical preparation according to the invention is advantageous in that the drug release is effected only from one or both faces thereof extending in the direction parallel to the layer plane, so that sustained pulsewise drug release can be attained.

The invention has been fully described in the foregoing description and examples included therein, but they may be altered or modified in various ways without departing from the spirit and scope of this invention.

We claim:

1. A sustained pulsewise-release pharmaceutical dosage form means for embedding beneath skin which embedded administration comprises (a) drug-containing polymeric material layers (layers A) and polymeric material layers free from the drug in question or containing only a slight and significantly smaller amount of the same (layers B) disposed alternatingly, and (b) a surface extending in a direction perpendicular to the layers and coated in its entirety with a polymeric material which is insoluble or scarcely soluble in water and in body fluids.

2. A pharmaceutical dosage form of claim 1, wherein the layers B contain no drug at all.

3. A pharmaceutical dosage form of claim 1, wherein layers B contain a drug which is different from the drug contained in layers A.

4. A pharmaceutical dosage form of claim 1, wherein the whole surface extending in a direction perpendicular to the layers and one face extending in a direction parallel to the layers are coated with a polymeric material which is insoluble or scarcely soluble in water and in body fluids.

5. A pharmaceutical dosage form of claim 1, wherein at least layers A or layers B comprise at least one member selected from the group consisting of collagen, gelatin, polylactic acid, polyglycolic acid and poly(lactide-co-glycolide).

6. A pharmaceutical dosage form of claim 1, wherein the polymeric material which is insoluble or scarcely soluble in water and in body fluids is a silicone polymer and covers the surface extending in a direction perpendicular to the layers.

7. A pharmaceutical dosage form of claim 1, wherein the drug is disposed in polymeric material layers, in a form of enclosed particles.

8. A pharmaceutical dosage form of claim 7, wherein the particles are liposome, microcapsules or microspheres.

9. A pharmaceutical dosage form of claim 7, wherein the particles are of a size which is generally within a range of from about 17 nm to about 1000 μm.

10. A pharmaceutical dosage form of one of claims 1–8, wherein the drug is a drug which is advantageously administered pulsewise.

11. A sustained pulsewise-release pharmaceutical dosage form of claim 1 which is adapted for embedded use beneath the skin, wherein the drug is one which is administrable by embedding beneath the skin and wherein layers B are substantially free from the drug.

12. A pharmaceutical dosage form of claim 1 wherein the polymeric material of each layer A and that of each layer B is degradable.

13. A pharmaceutical dosage form of claim 6 wherein the silicone polymer also covers a surface extending in a direction parallel to the layers.

14. A sustained pulsewise-release pharmaceutical tablet means for embedding beneath the skin and administration comprising a plurality of substantially planar parallel layers surrounded by a surface perpendicular to the layers; said layers being of at least two different types: a first type comprising drug-containing polymeric material and being disposed alternatingly with a second type containing polymeric material which is free from or substantially free from the drug in the first type; the surrounding perpendicular surface being coated with a polymeric material which is insoluble or substantially insoluble in water and in body fluids.

15. A sustained pulsewise-release pharmaceutical dosage form which comprises (a) drug-containing polymeric material layers (layers A) and polymeric material layers free from or substantially free from the drug in question (layers B) disposed alternatingly, and (b) a surface extending in a direction perpendicular to the layers and coated in its entirety with a polymeric material which is insoluble or scarcely soluble in water and in body fluids; the pharmaceutical preparation being in a form suitable for and the drug being one which is administrable by being embedded beneath the skin.

16. A dosage form of claim 1, claim 14, or claim 15 in which the drug is a peptide protein type drug for embedded use and which is unstable to heat and to organic solvents.

17. A pharmaceutical dosage form of claim 1, wherein the drug is GRF (1-29).

18. A pharmaceutical dosage form of claim 1, wherein peptide protein type active substance is interferon.

19. An implantable pharmaceutical preparation of one of claims 1–8, wherein the layers A and layers B are layers formed by compression molding.

20. A method of pulsewise administering a pharmaceutical which comprises embedding a dosage form beneath the skin of a host in need of such therapy, and wherein the dosage form is a sustained pulsewise-release pharmaceutical dosage form which comprises (a) drug-containing polymeric material layers (layers A) and polymeric material layers free from the drug in question or containing only a slight and significantly smaller amount of the same (layers B) disposed alternatingly, and (b) a surface extending in a direction perpendicular to the layers and coated in its entirety with a polymeric material which is insoluble or scarcely soluble in water and in body fluids.

* * * * *

UNITED STATES PATENT AND TRADEMARK OFFICE
CERTIFICATE OF CORRECTION

PATENT NO. : 5,011,692
DATED : April 30, 1991
INVENTOR(S) : Fujioka, et al.

It is certified that error appears in the above-identified patent and that said Letters Patent is hereby corrected as shown below:

Column 4, line 10, "eruthromycin" should read --erythromycin--.
Column 8, line 59, "for embedding beneath skin, which" should read --for--; line 60, "comprises" should read --beneath skin, which comprises--. Column 9, line 46, "skin and" should read --skin--; line 47, "comprising" should read --and comprising--.
Column 10, line 22, "peptide protein" should read --peptide· protein--; line 28, "peptide protein type active substance" should read --the drug--.

Signed and Sealed this

Tenth Day of November, 1992

Attest:

DOUGLAS B. COMER

Attesting Officer     Acting Commissioner of Patents and Trademarks